United States Patent [19]

Farquharson et al.

[11] Patent Number: 5,464,444
[45] Date of Patent: Nov. 7, 1995

[54] ATTACHMENT FOR ARTIFICIAL ARM PROSTHETIC DEVICE

[76] Inventors: Ronald H. Farquharson, Rte. 3, Box 3866 CR 628, Brazoria, Tex. 77422; Danny P. Still, Rte. 5, Box 5, Angleton, Tex. 77515

[21] Appl. No.: 216,624

[22] Filed: Mar. 23, 1994

[51] Int. Cl.⁶ .................. A61F 2/54; B25J 17/00
[52] U.S. Cl. .................. 623/65; 623/61; 623/62; 901/28; 901/29
[58] Field of Search ................ 623/61, 62, 65; 901/28, 29; 74/89.14

[56] References Cited

U.S. PATENT DOCUMENTS

| | | | |
|---|---|---|---|
| 1,206,753 | 11/1916 | Desmore | 623/65 |
| 1,213,222 | 1/1917 | McKay | 623/65 |
| 1,278,106 | 9/1918 | Carson | 623/65 |
| 1,299,543 | 4/1919 | Bowler | 623/65 |
| 1,310,589 | 7/1919 | Trautman | 623/65 |
| 1,692,073 | 1/1928 | Brenner | 74/89.14 |
| 2,561,523 | 7/1948 | Lux | 623/65 |
| 2,566,375 | 7/1950 | Rocklin | 623/65 |
| 3,036,312 | 2/1960 | Larson et al. | 623/65 |
| 3,490,078 | 4/1970 | Perez | 3/12.8 |
| 3,747,128 | 7/1973 | DeFilipo | 623/65 |
| 3,802,302 | 11/1974 | Bengston | 81/177 |
| 3,942,194 | 3/1976 | Winter . | |
| 4,357,717 | 11/1982 | Puhl | 623/65 |
| 4,661,113 | 4/1987 | Adkins | 623/65 |
| 4,944,765 | 7/1990 | Keith | 623/65 |
| 5,163,966 | 11/1992 | Norton et al. | 623/65 |

FOREIGN PATENT DOCUMENTS

| | | | |
|---|---|---|---|
| 0484160 | 9/1917 | France | 623/65 |
| 0306713 | 7/1918 | Germany | 623/65 |
| 0323435 | 7/1920 | Germany | 623/65 |
| 0845095 | 7/1952 | Germany | 623/65 |
| 0100582 | 8/1923 | Switzerland | 623/65 |

OTHER PUBLICATIONS

High Tech for the Handicapped pp. 78–79 (1991) by Larry Kettelkamp, Enslow Publishers, Inc. N.J.

Primary Examiner—David H. Willse
Assistant Examiner—Bruce E. Snow

[57] ABSTRACT

A terminal device is described which is attachable to the end of a prosthesis on an arm and there serves as an attachment site for a variety of tools or implements designed to mate with the terminal device. The terminal device comprises a first main part in operable and pivotal combination with a second main part, the combined main parts providing on one end a device for attaching to the end of an arm prosthesis, and on the other a device for attaching a variety of implements, the said device for implement attachment providing articulation capabilities that allow positioning of the implements in a variety of positions relative to the position of the arm prosthesis. Among the implements which can be attached are for example: cutting tools (such as saws, files, knives, scrapers, and awls); various wrenches (such as open end wrenches, closed end wrenches, ratchet wrenches, adjustable wrenches, Allen wrenches, and pipe wrenches); and a variety of other implements such as spoons, scoops, spatulas, planes, brushes, fishing rods, and stirring devices.

12 Claims, 11 Drawing Sheets

ATTACHMENT FOR ARTIFICIAL ARM PROSTHETIC DEVICE

FIELD OF THE INVENTION

Attachment for an artificial arm prosthesis providing connection thereto with a variety of connectable implements.

BACKGROUND OF THE INVENTION

There have been a number of prosthetic devices for use by amputees who have lost at least one or both hands, or one or both arms. Many of the devices are body powered and some are driven, or at least assisted, by electrical, myoelectrical, and/or pneumatic means. Many of the sophisticated devices are very expensive to manufacture and repair.

There are commonly used devices which attach to a prosthesis fastened to the remaining part of an arm on which a hand is missing and in which the device (sometimes called a "cup" or "cuff") at the end is designed to accept certain tools that are mechanically, but removably, attached to the cup. Such "cups" or "cuffs" can be an attachment position at the end of an expensive, complex prosthesis, or a relatively inexpensive, simple prosthesis.

U.S. Pat. No. 3,490,078 (Perez) discloses a flexible sleeve for a forearm stump which has a threaded female member at the end of the sleeve into which can be threaded a handle of a tool.

U.S. Pat. No. 3,802,302 (Bengtson) discloses a tool holding prosthetic device having a threaded connector devices for attaching various tools and shows the use of a detent ball.

U.S. Pat. No. 3,942,194 (Winter) discloses a device for attaching to a hand to which an implement can be removably fastened U.S. Pat. No. 4,661,113 (Adkins) discloses a device which is attachable to to an amputee's prosthesis to enable the amputee to swing a golf club or other device which requires swinging.

U.S. Pat. No. 5,163,966 (Norton et al) discloses a prosthetic limb having a means for grasping and holding a bar or tubular member.

U.S. Pat. No. 4,944,765 (Keith) discloses an artificial arm prosthetic drive device for holding a rotatable tool.

In *High Tech For The Handicapped* by Larry Kettelkamp, published by Enslow Publishers, Inc. Hillside, N.J., 1991, there is described a prosthesis called the "Utah Arm", shown in exploded view, which illustrates a wrist rotator which has annular threads for receiving the threaded extension of gripping devices or artificial hand that is interchangeable and operates on a battery pack.

There is a perceived need for ways and means that permit the wearer of an arm prosthesis to have enhanced capabilities in the type and operation of mechanically attached implements.

The present invention is directed principally to providing for mechanical attachments of implements to prosthetic devices which are adaptable for movement by the wearer, using mechanical, pneumatic, electrical, or electromechanical movement of implements removably affixed to the end of a arm.

Throughout this disclosure the expression "terminal device" is used in the ordinary vernacular of arm prostheses as a device added to an arm prosthesis at a wrist location.

The terms "tool connector" and "tool coupler" refer to parts which are used for coupling the tool with the terminal device. "Tool" and "implement" each refer to the item being coupled with the terminal device.

SUMMARY OF THE INVENTION

This invention comprises a terminal device which is releasably attachable to the end of an arm prosthesis where it serves as an attachment site for a variety of tools or implements designed to mate with the said terminal device. The terminal device comprises a first main part in operable combination with a second main part, having on one end a means for attachment to the end of an arm prosthesis, and on the other end a means for attaching a variety of implements, the said terminal device being operable in providing means for implement attachment providing articulation capabilities that allow positioning the implements in a variety of positions relative to the position of the arm prosthesis.

BRIEF DESCRIPTION OF THE DRAWINGS

FIGS. 1–8b, not drawn to any particular scale, are presented as visual aids in relating embodiments the invention.

FIGS. 9A–9E are included as visual aids in relating a particular embodiment of the present invention as discussed in an Example which follows below.

DETAILED DESCRIPTIONS INCLUDING BEST MODE CONTEMPLATED

A terminal device is described which is attachable to the end of an arm prosthesis which serves as an attachment site for a variety of tools or implements designed to mate with the device. The device comprises a main part which has on one end a means for attachment to the end of an arm prosthesis, and on the other a means for attaching a variety of implements, the said means for implement attachment providing articulation capabilities that allow positioning the implements in a variety of positions relative to the position of the arm prosthesis. Among the implements which can be attached are for example: cutting tools (such as saws, files, knives, scrapers, and awls); various wrenches (such as open end wrenches, closed end wrenches, ratchet wrenches, adjustable wrenches, Allen wrenches, and pipe wrenches); and a variety of other implements such as brushes, fishing rods, spoons, scoops, spatulas, planes, and stirring devices.

Of particular interest in applying the terminal device of this invention is an arm prosthesis having a "cup" or wrist unit at its outer extremity which has an annular threaded opening into which a threaded part of a hook or clamp-like device can be screwed. Such clamp-like devices often have an attachment means to which a cable can be attached which is remotely actuated by an actuator to pull the cable and force open the hook or clamp jaws. Upon releasing the force which pulls the cable, the clamp jaws close again in response to a resilient force, such as a spring or rubber band. As will be seen below, this invention is very adaptable for use in replacing, at appropriate times, the clamp-like device in order to perform tasks for which the clamp-like device is not well-suited. The present invention even provides, as an option, an attachment means for securing the cable to prevent the cable from just hanging loose, though the cable may not be needed for the particular implements being used with the present invention.

One may consider the invention as a terminal device for releasable attachment to the end of an arm prosthesis in providing means for holding an implement in a variety of positions relative to the arm prosthesis, said device comprising a structure having a first main part with a fore end and an aft end, the fore end being designed for releasable attachment to the end of an arm prosthesis, and the aft end being designed for combination with a second main part, said second main part having a fore end and an aft end, the fore end being affixed to the aft end of said first main part with pivotable means for provide a plurality of positions relative to the arm prosthesis, and operative to form an integral implement-holding device, and the aft end of the second main part being designed for releasable attachment of an implement coupling part.

A preferred embodiment of the terminal device involves the pivotable means provided by a worm gear mounted within, and traversing, the first main part in a direction normal to the fore-aft axial alignment thereof, said worm gear communicating with an arcuate toothed fore end of said second main part, said worm gear being revolvable by means visibly mounted at one end of said worm gear. The travel limit of the toothed fore end is limited by stop means to avoid having the toothed fore end turn completely out of operable connection with the worm gear. The teeth of the toothed fore end of the second main part is matched with the threads of the worm gear.

Another preferred embodiment of the terminal device is that of providing the aft end of the second main part with a hollow end for insertion of a tool holding member, herein also called a tool copling part.

Another preferred feature of the device is having the first main part with a threaded extension on its fore end for threading into a threaded receptacle of matching size and threads, said receptacle being located at the end of an arm prosthesis. This will probably be the more inexpensive method for amputees who already have a prosthesis which has a threaded receptable.

An even more preferred means of have the terminal device attachable to an arm prosthesis is a releasable attachment device shown in FIG. 2a and described more fully below.

Furthermore, a preferred feature is that of having the first main part comprise a circular body of length greater than width, having a cutaway portion across its breadth of a size operable for closely fitting an inserted toothed arcuate fore end portion of the second main part, said inserted toothed arcuate portion being in operable contact with a worm gear installed traversing the first main part within the foremost location of the cutaway portion.

Figure 1:
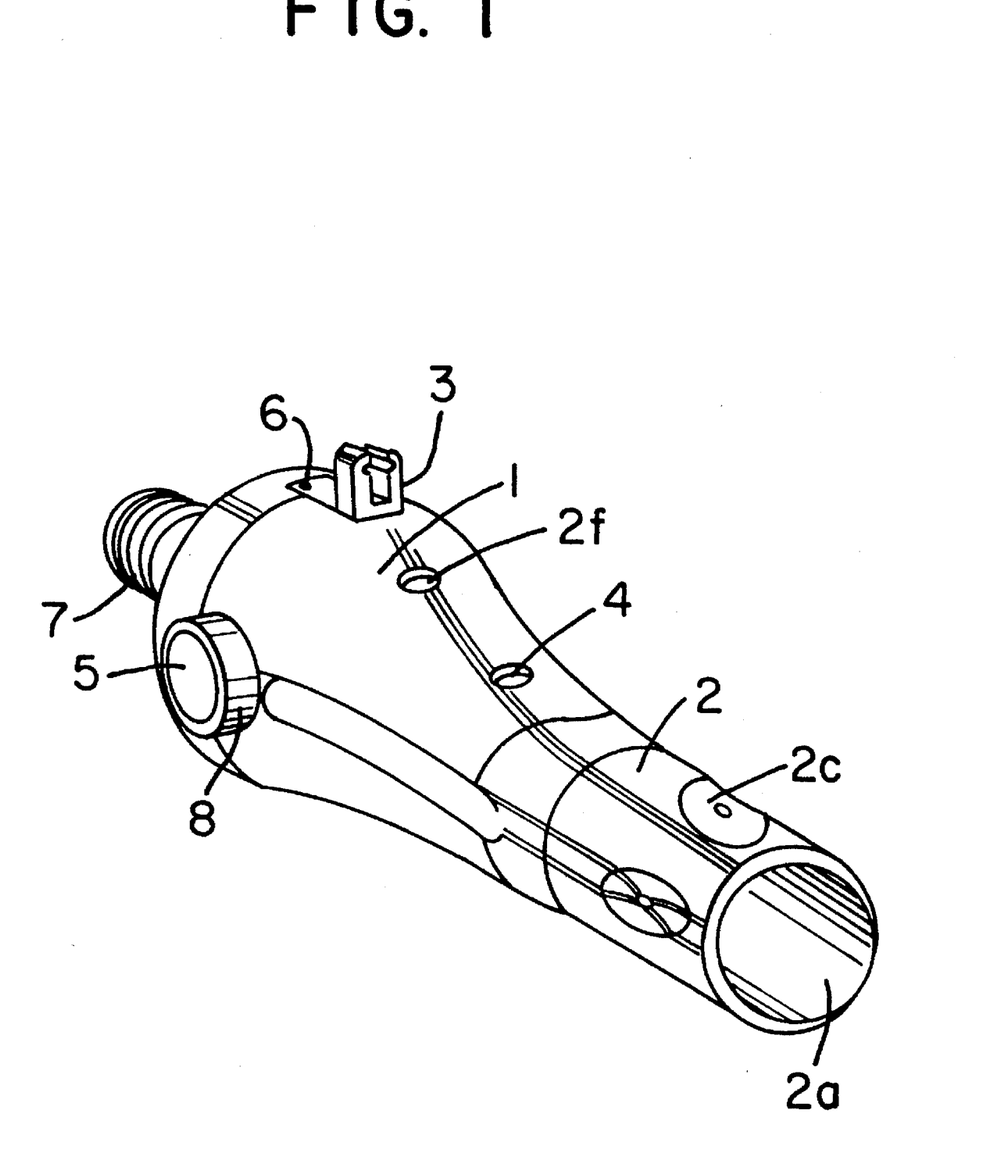
FIG. 1 illustrates a perspective view of a terminal device having a first main part 1, which has a threaded end 7, combined with a second main part 2, which has a hollow end 2a that is positioned distal to threaded end 7.

Further descriptions of the invention and of the drawings are presented below:

FIG. 1 illustrates a perspective view of the terminal device having a first main part 1, having a threaded end 7, combined with a second main part 2 having a hollow end 2a which is distal to threaded end 7. There is shown (as an optional feature) a cable holder 3 fastened to first main part 1 with screws 6; the optional cable holder is made available in the event the wearer of the arm prosthesis also, at times, uses a clamp-like implement at the end of the arm prosthesis which requires a cable for opening the clamp. The present invention does not require the cable, but part 3 is useful for holding the end of the cable to avoid having it hang loose. Also identified by numbers in FIG. 1 is a fastener 4 which holds second main part 2 in place in first main part 1. Part 5 is the head of an revolvable worm gear, adaptable to be turned using a screw driver or Allen wrench or the like, which is functional in cooperating with the hidden end of second main part 2 to adjust the positioning of part 2, as it is purposely pivoted at fastener 4 when worm gear 5 is turned in either direction. Shown encircling the head of worm gear 5 is a tightly fitting knurled ring which is quite handy in that the knurled ring 8 can be turned by hand and that turns the worm gear. The hollow portion 2a of second main part 2 functions as a receptacle for insertion of a tool holder having a releasable locking device such as a detent ball or ball plunger, preferably as described in greater detail in FIG. 8, which cooperates with a hole in a concave indentation 2c of the second main part to hold the tool in place. Other types of springs and easily released connecting means can be used. In FIG. 1 there is shown an end of a travel limiting peg 2f which traverses through the portion of second main part 2 when it is installed there. The peg cooperates with an arcuate slot 2e (shown in FIG. 2) cut through second main part 2, the slot being of a length predetermined to provide a travel limit of second main part 2 when turned by worm gear 5 to avoid having the worm gear move the fore end of second main part 2 too far out of the side of first main part 1. The slot is disclosed in FIG. 2 and the peg 2f is shown in FIG. 2 and is seen in cross-section in FIG. 3.

Figure 2:
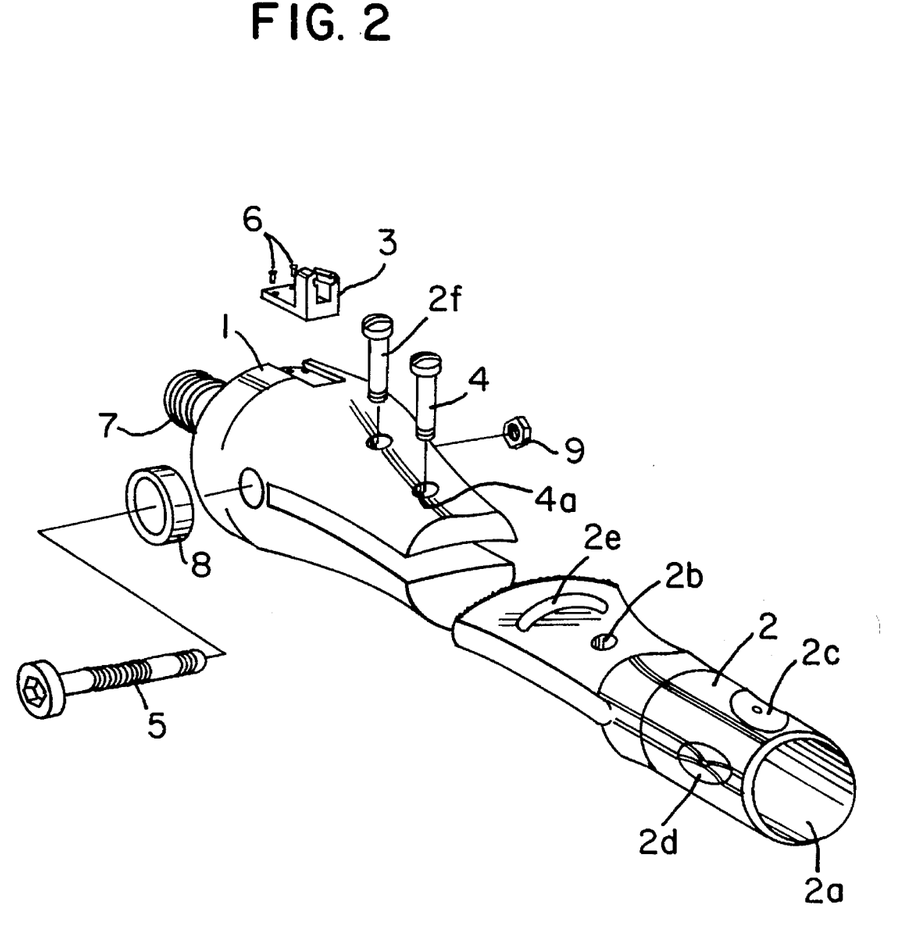
FIG. 2 illustrates an exploded view of the perspective view of FIG. 1, showing first main part 1 and second main part 2 as separable parts.

FIG. 2 illustrates an exploded view of the perspective view of FIG. 1, showing first main part 1 and second main part 2 as separable pars. Note that the end of second main part 2 has teeth along its arcuate end which are designed to mesh with the worm gear 5, so that when worm gear 5 is turned, either direction, then part 2 is caused to pivot on screw fastener 4; the fastener 4 also holds second main part 2 in place in first main part 1. Also shown in FIG. 2 is screw nut 9 which mates tightly with the end of worm gear 5 and turns with worm gear 5 when it is turned by the use of the knurled ring 8 or by using a wrench or screw driver at the end of worm gear 5. Also shown is hole 4a through which screw 4 is positioned and when second main part 2 is assembled into first main pan 1. An arcuate slot 2e is shown which, when second main part 2 is assembled into operable position in first main part 1, cooperates with peg 2f applied through hole 4b to limit the travel of second main part when operated by the worm gear 5 in contact with the arcuate toothed end of second main part 2. Also in FIG. 2 there is shown the optional cable holder 3 and fasteners 6 which hold it in place on first main part 1

Figure 2A:
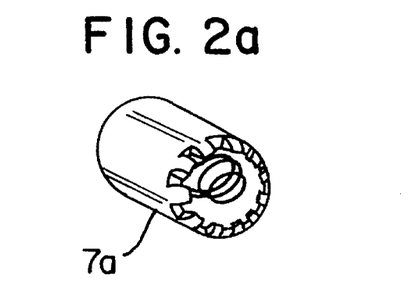
FIG. 2a illustrates an alternative part 7a which can be used in place of threaded part 7 at the fore end of first main part 1 for connection to the outer end of an arm prosthesis which is equipped with mating for a such a device.

FIG. 2a shows a commercial coupling device knows as the HOSNER Wrist Unit* (*a name used in the trade) which is known in the prosthesis industry; it is useful in this invention in place of the threaded extension on the fore end of first main part 1. It can be seen that it has a row of short protrusions which form notches around the perimeter of the coupling end, the protrusions being bent inwardly for cooperating with mating projections in the cuff of an arm prosthesis. There is a spring in the center which provides the force for maintaining the coupling of the mating projections. The operation of this wrist unit is well known and it adds versatility to a terminal device in providing 360° of indexed rotation for the terminal device, the rotation being accomplished by compressing a release button on the exterior of the prosthesis "cup" or cuff which permits the terminal device to be turned one or more "notches" while the button is depressed. The button is also used in totally releasing the terminal device from engagement with the arm prosthesis.

Figure 3:
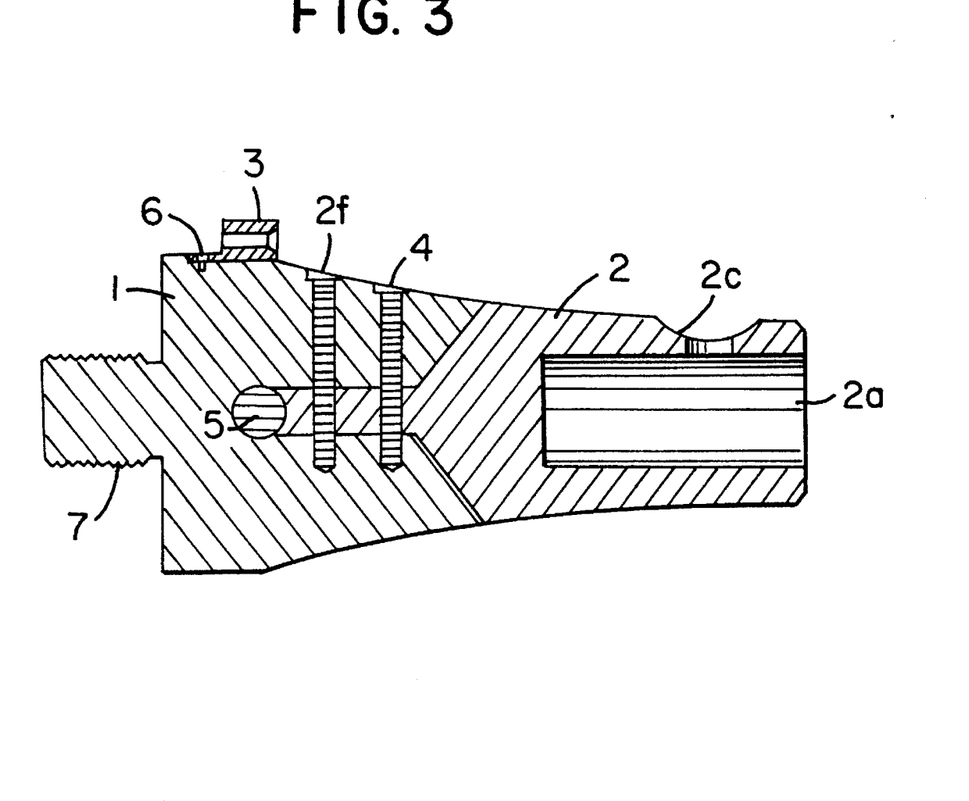
FIG. 3 is a cross-section of the terminal device comprising first main part 1 united with second main part 2.
Figure 8:
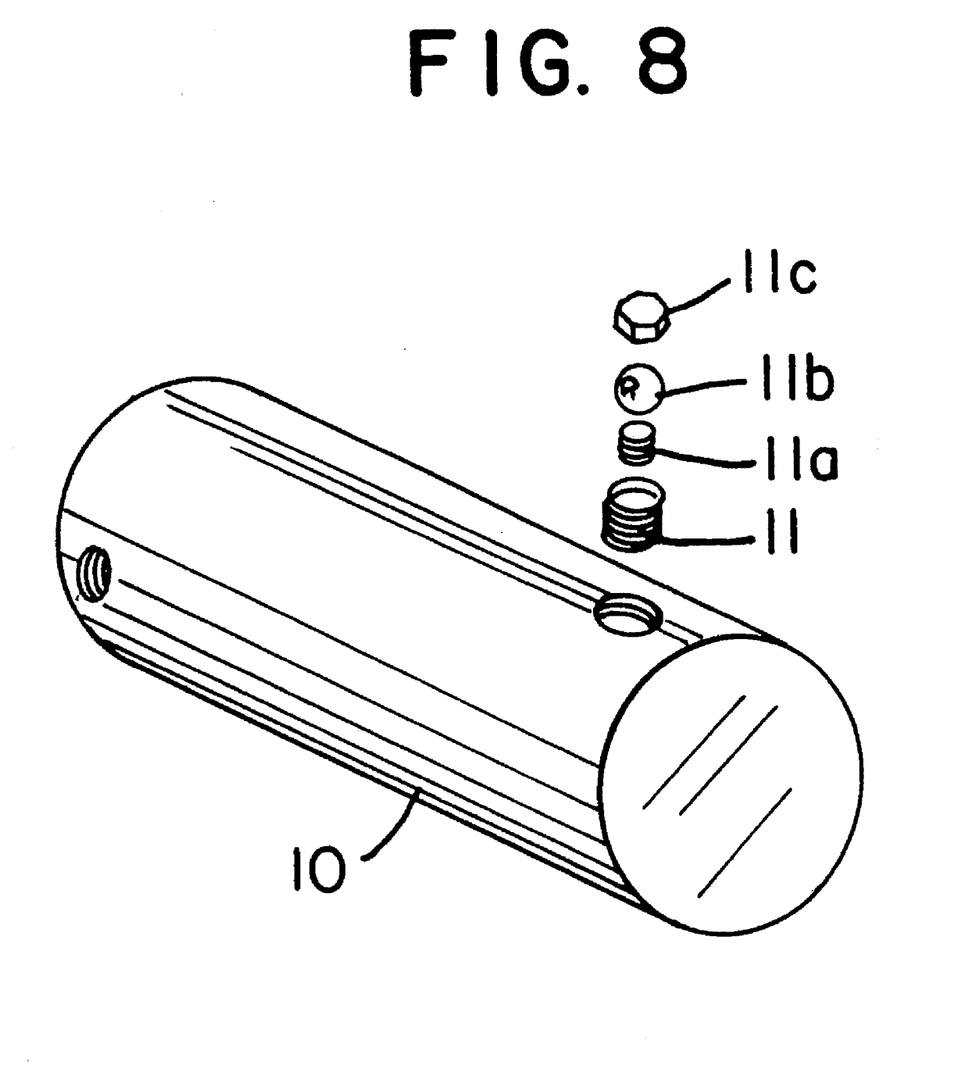
FIG. 8 shows a tool coupler 10 in which fastener 11 is shown as a detent ball (sometimes called a "ball plunger", in exploded view as parts 11a, 11b, and 11c, and as 11 when in operable position when implement coupler 10 is mounted onto implements such as in FIGS. 8a and 8b, and ready to be inserted into a terminal device of FIG. 1–4.

FIG. 3 is a cross-section view of the terminal device comprising first main part 1 united with second main part 2. In this view it can be seen that second main part 2 engages worm gear 5 and is held in place by screw 4 which is positioned in first main part 1 and extending through a hole in second main part 2. In addition to holding second main part 2 in position in first main part 1, screw 4 also provides a secure pivot point for the turning from side to side of second main part 2 upon revolving the worm gear, either way and then back again, as needed to attain the desired attitude of second main part 2 with respect to an arm prosthesis on which the terminal device is attached. Also shown is a coupling hole 2c which penetrates through a concave indentation in part 2, and into hollow part 2a. This coupling hole 2c is of a dimension which permits a small spring loaded ball to jut into it from within the hollow part 2a, but which can pressed back out of the hole with properly applied pressure. The invention is not limited to having only one coupling hole, but there can be as many as the spacing around the perimeter of second main part 2 permits whereby an inserted tool, which has a spring loaded ball for coupling with hole 2c can be located to the best advantage. Such spring loaded balls, such as shown in detail in FIG. 8 are often called "ball plungers" by skilled mechanical craftsmen and engineers. Also shown in the cross-section view is peg 2f passing through slot 2e.

Figure 4:
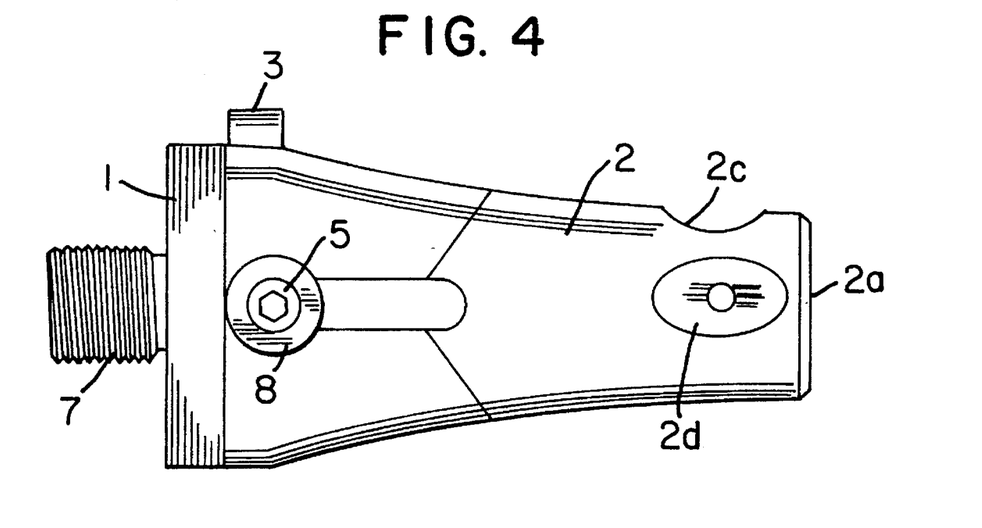
FIG. 4 is a plan view of the terminal device which is shown in perspective in FIG. 1 and in cross-section in FIG. 3.

FIG. 4 is a plan view of the device which is shown in perspective in FIG. 1 and as shown in cross-section in FIG. 3. Here the parts 1, 2, 2a, 2c, 2d, 3, 5, 7, and 8 are shown, and also there is indicated a second coupling hole 2d to illustrate that a plurality of coupling holes can used.

Figure 5:
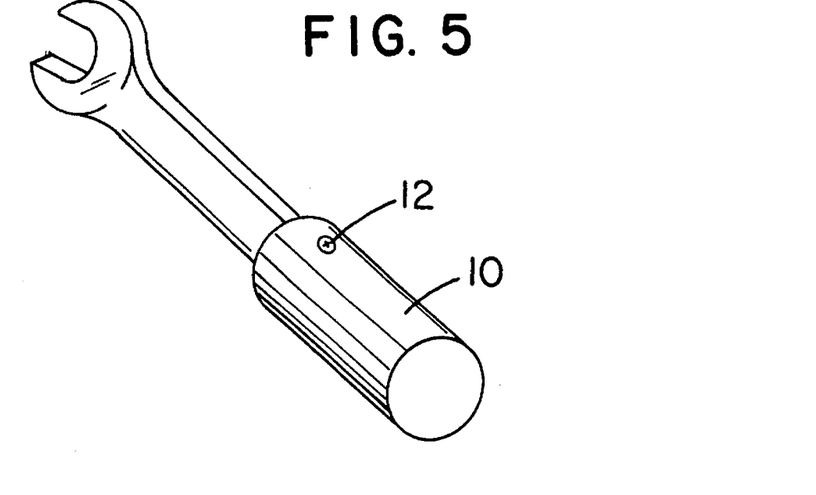
FIGS. 5, 5a and 5b show examples of certain commonly used wrenches which, when combined with, equipped with, or manufactured with tool coupler 10, are insertable into hollow end 2a of second main part 2 shown in FIGS. 1–4.
Figure 5A:
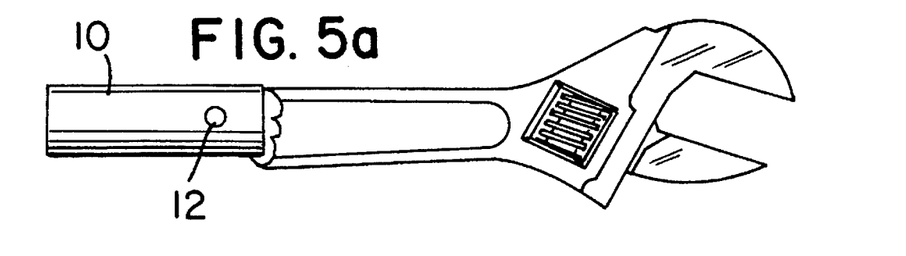
Figure 5B:
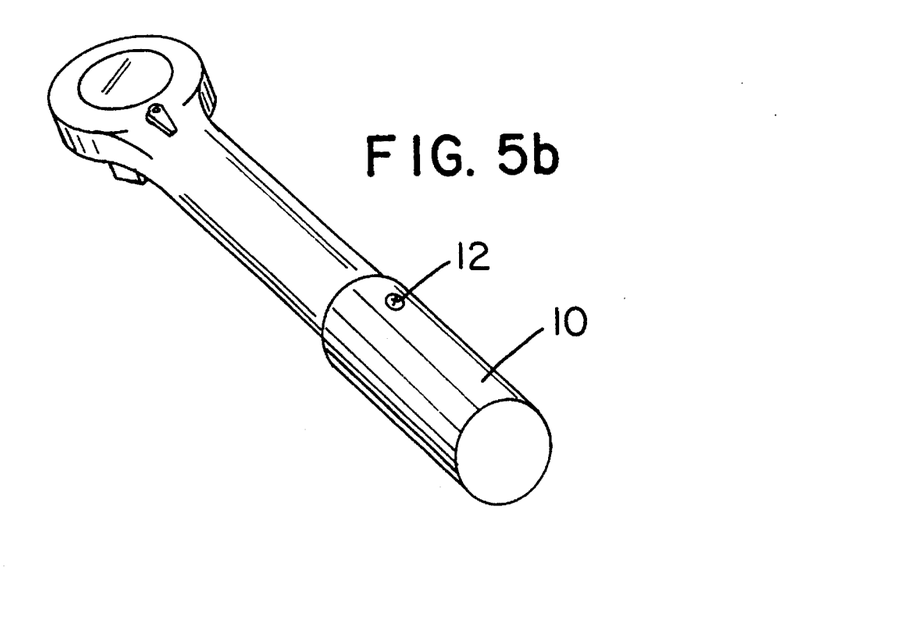

FIGS. 5, 5a, and 5b show examples of certain commonly used wrenches which, when combined with part coupling part 10, are insertable into hollow end 2a of second main part 2 shown in FIG. 1 and elsewhere. In order to fit into part 2, it is sometimes necessary to modify the handle of the implement for adapting the coupling part 10 or even to weld the handle in place to the coupling part 10. FIG. 5a, for example, demonstrates a welded piece onto an adjustable wrench which is inserted into coupling 10 and held there by set screw 12.

Figure 6:
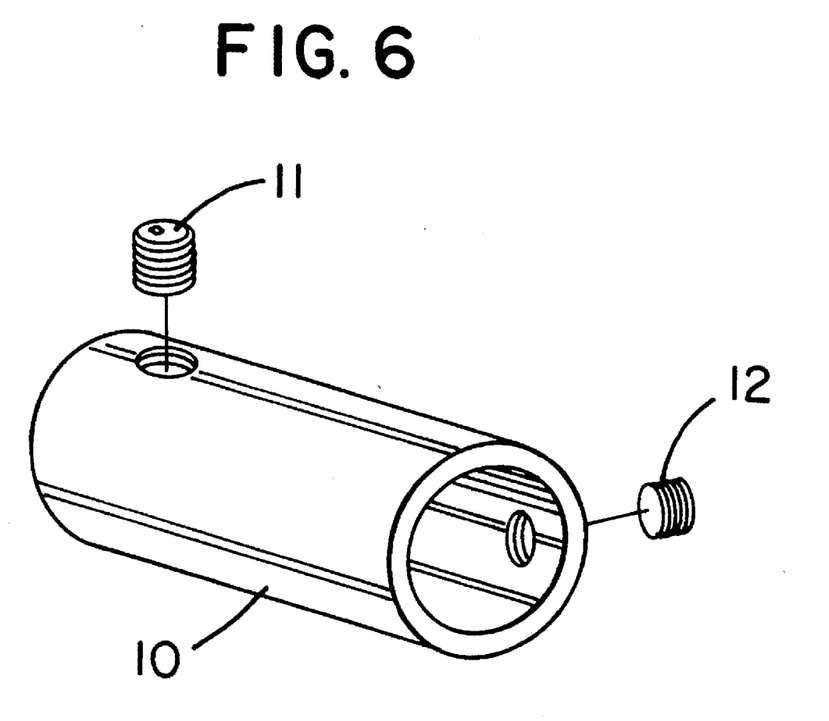
FIG. 6 shows tool coupler 10 which is of a size appropriate for insertion into hollow portion 2a of second main part 2 of the device shown in FIGS. 1–4, and for being fastened there by coupler fastener 11, shown poised outside its receptacle; also it is shown that tool coupler 10 has a hollow end for receiving an insertable implement which can be held in place by implement fastener 12, shown poised outside its receptacle.

FIG. 6 shows implement coupling part 10 which is of a size, on at least one end, appropriate for insertion into hollow portion 2a of second main part 2 of the device shown in FIGS. 1–4, and for being fastened there by spring-loaded coupling device 11; also it is shown that implement coupling part 10 has a hollow end for receiving an insertable implement which can be held in place by fastener 12 such as a set screw or rivet, or the like. At times, it may be necessary to modify a tool handle to make it insertable in, or attachable to, coupling part 10. Welding or clamping of tools to coupling part 10 is within the scope of the concept of this invention. It is also envisioned here that the coupling part 10 need not have the same dimensions on both of its ends, since those dimensions can be adapted to the particular implement and terminal device involved.

Figure 7:
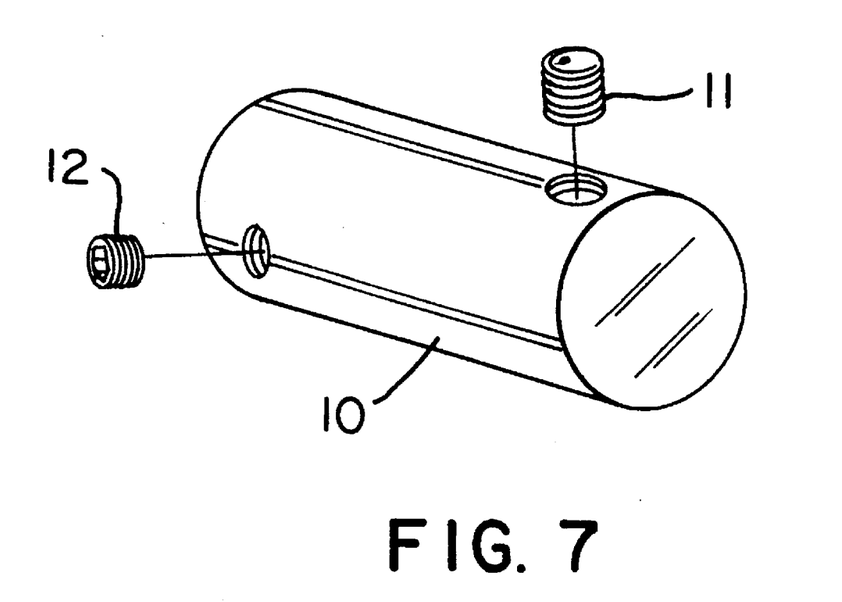
FIG. 7 also shows tool coupler 10, but with a closed end in view, along with implement fastener 12 and coupler fastener 11, both of which are shown in exploded view from their respective positions in tool coupler 10.

FIG. 7 also shows part 10, but with a closed end in view, along with spring-loaded coupling device 11 and fastener 12.

Regarding the spring-loaded coupling device 11 of FIGS. 6 and 7, a detailed view of it can be seen in FIG. 8.

Figure 8A:
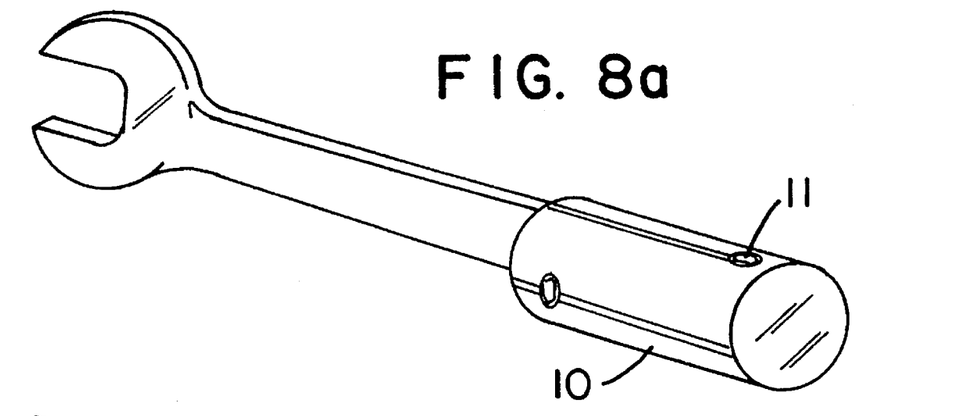
Figure 8B:
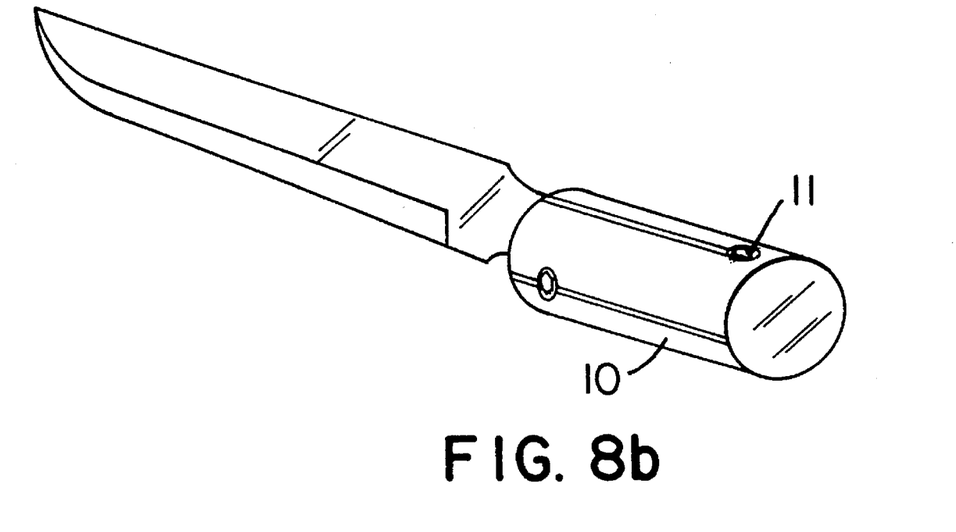

FIG. 8 shows tool coupling part 10 in which spring-loaded snap-in device 11 is shown in exploded view as spring 11a, ball 11b, and retainer ring 11c, which are poised for being pressed into position inside externally threaded plug 11d, which is poised for being screwed into a receiving hole in part 10. The spring-loaded snap-in devices, also known as "ball-plungers", are indicated simply as part 11 in FIGS. 8a and 8b. When part 11 is in operable position on coupling part 10, and coupling part 10 is mounted onto an implement, it is ready to be inserted into hollow part 2a of the device of FIG. 1 and 3 by pushing it in where the ball plunger operates with hole 2c. It will be understood, of course, that the position of spring-loaded coupling device 11 on the part 10 should be a position which permits it to cooperate with hole 2c on part 2 which is seen in FIGS. 1 and 3.

FIGS. 9a–9E are included as visual aids in relating a particular embodiment of the present invention, as discussed below.

EXAMPLE

Figure 9A:
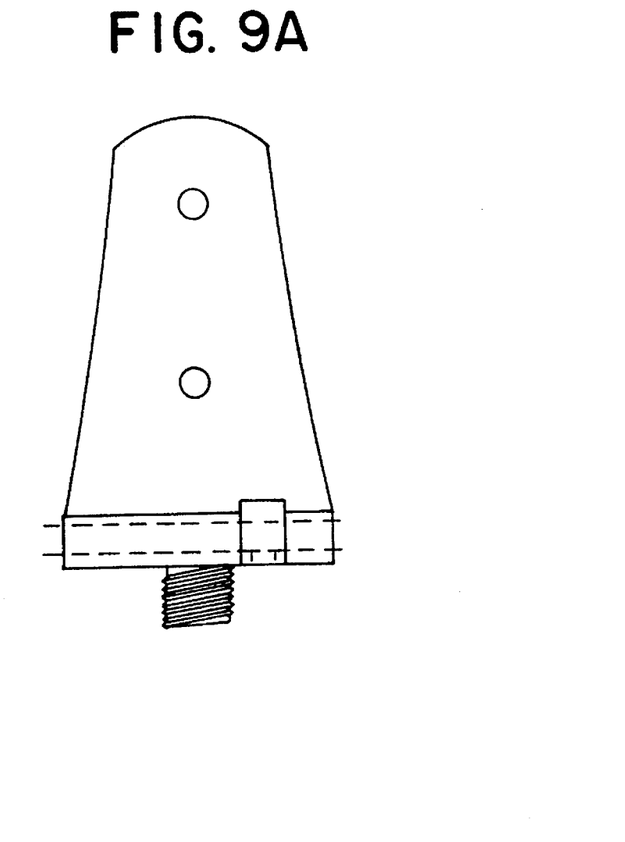
FIGS. 9A–9E are visual aids for describing and illustrating certain embodiments, showing the dimensions of parts.
Figure 9B:
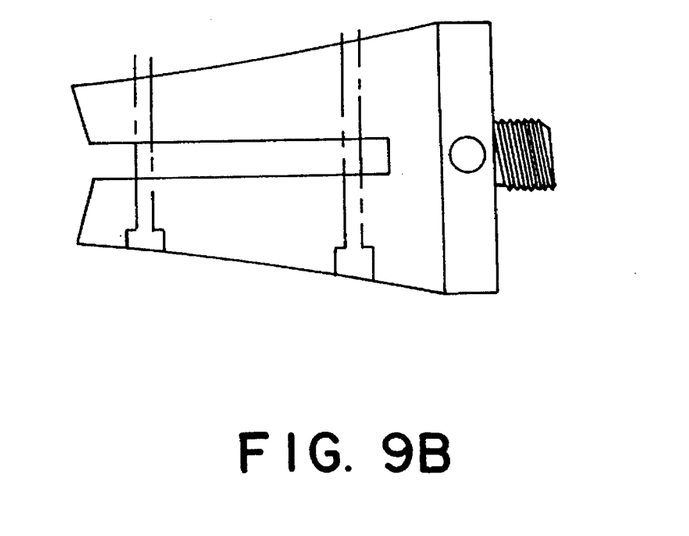

With reference to FIG. 9A there is a first side view of the first main part which has a threaded ½ inch wide protrusion for mounting onto a threaded receptacle of an arm prosthesis and a second side view FIG. 9B taken normal to the first side view. Also in FIG. 9E there is shown a worm gear of appropriate dimensions for insertion through said first main part, a knurled ring for encircling one end of the worm gear, a retainer sleeve for attachment to the other end of the worm gear and a fastener for holding the worm gear in place, when installed through said first part which is shown as an end view between the worm gear and the sleeve. Also shown in FIG. 9E are two side views, normal to each other, to illustrate the cable attachment, which, as stated herein above, is helpful to have but which is optional and not essential to the operation of the invention.

Figure 9C:
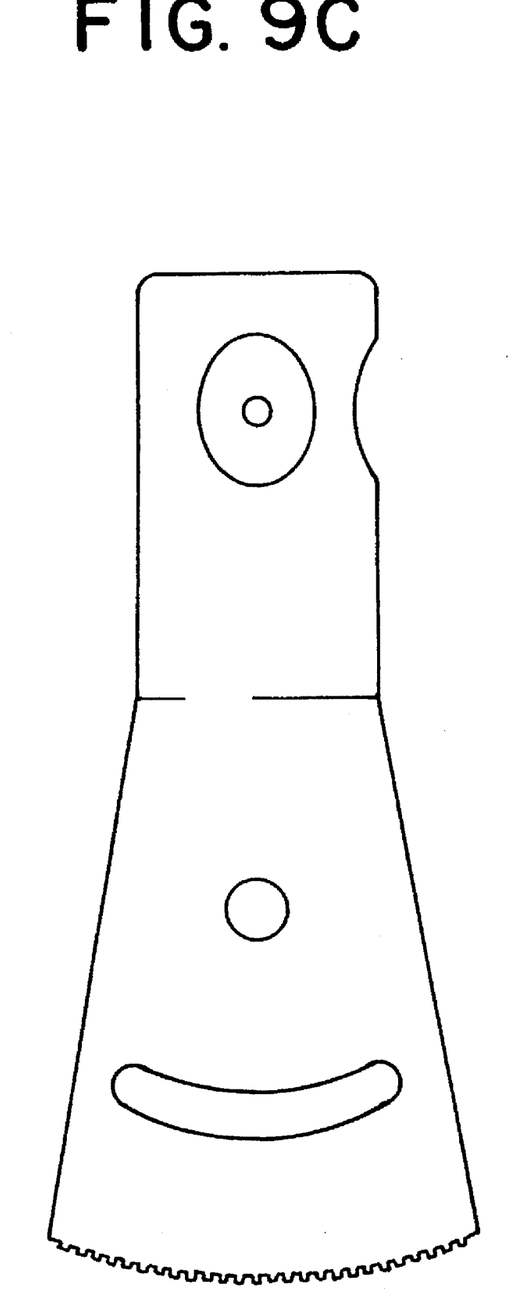

FIG. 9C shows a top view of the second main part discussed herein before, and a side view of that part. In the top view the wide area has an arcuate edge which has a large number of teeth designed to cooperate with the worm gear shown in FIG. 9E to cause the second part to move pivotally around a fastener which, in operation of a completely assembled device, will pass through the hole shown in that wide area. Also seen in the top view is a convex indentation, seen as a round wide area, which has a hole through it to the interior of the second main part. When a tool is inserted into hollow portion of the second main part, that hole cooperates with the spring-loaded coupling device which is part of the tool holder. The spring-loaded coupling device can be disconnected to release the tool by mashing down on the spring-loaded ball or by twisting the tool, or yanking it, to cause the ball to be squeezed out of the hole.

Figure 9D:
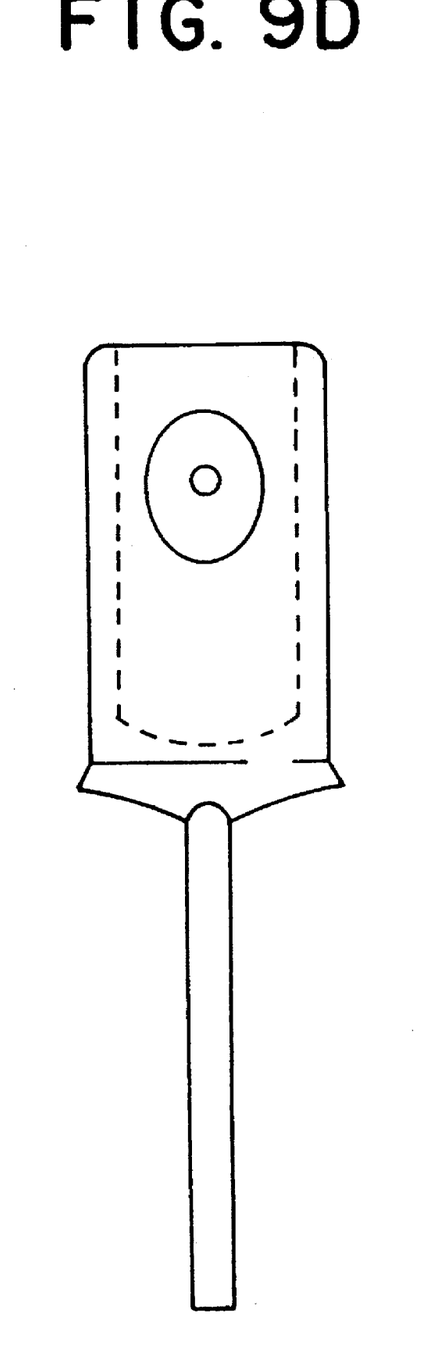
Figure 9E:
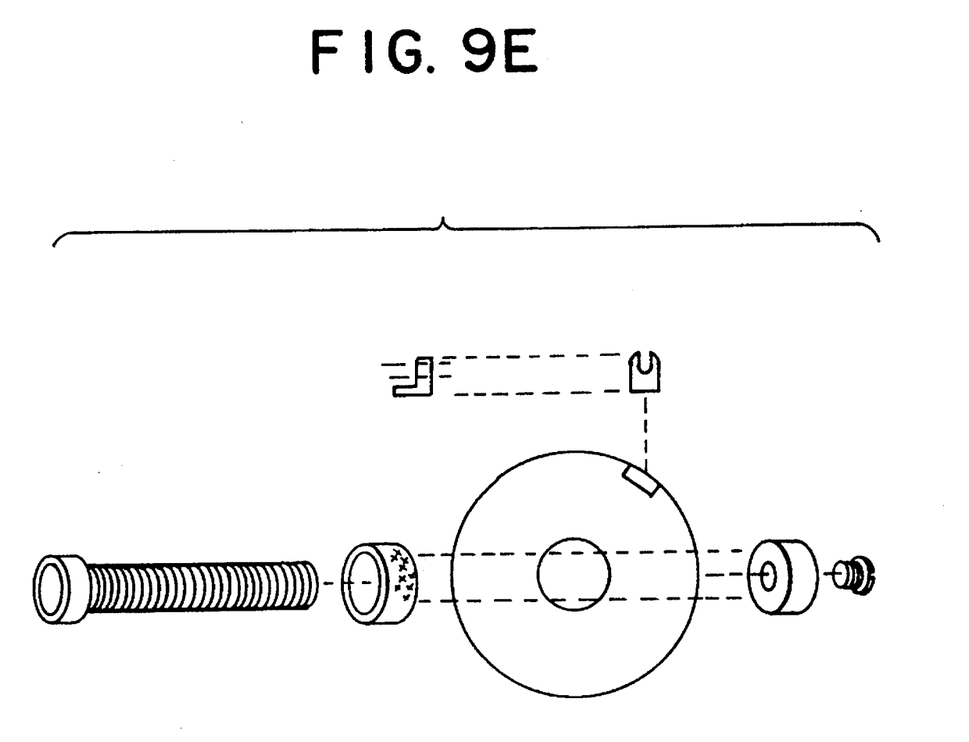

Also in FIG. 9D is a side view illustration of the second main part, with an indication at one end of the teeth (shown on arcuate edge of the wide area in the top view) and at the other end a graphic illustration of the size of a tool holder inserted into the hollow portion of the second main part. Traversing almost across the wide area in the top view of FIG. 9C is an arcuate slot through which a peg is inserted when the first main part and the second main part are fitted together. This limits the lateral movement of the second main part so that it will not be moved too far by the action of the worm gear turning it.

There are, of course, a range of sizes and relative dimensions which one may employ in the practice of this invention and practitioners of these relevant arts, having learned of this disclosure, may devise embodiments other than those specifically described or referred to in this disclosure without departing from the concepts proscribed by the claims which follow.

What is claimed is:

1. A terminal device for releasable attachment to the end of an arm prosthesis in providing means for coupling with an implement in a variety of positions relative to the arm prosthesis, said terminal device comprising a structure having a first main part with a fore end and an aft end, the said fore end releasably attach to the end of an arm prosthesis, and the said aft end being operably affixed to a second main part pivotably mated into a slotted opening traversing the aft end of the first main part, said second main part having a fore end and an aft end, its fore end being affixed to the aft end of said first main part with pivotable means for providing a variety of stationary positions relative to the arm prosthesis, and operative to form an integral device, the aft end of the second main part having a hollow end for releasable insertion therein of an implement by means of an implement coupling part, wherein the pivotable means is provided by a worm gear mounted within, and traversing, the first main part in a direction normal to the fore-aft axial alignment thereof, said worm gear communicating with an arcuate toothed fore end of said second main part, said worm gear being revolvable by means visibly mounted at one end of said worm gear.

2. The terminal device of claim 1 wherein the first main part has a threaded extension on its fore end for threading into an annular threaded receptacle of matching size and threads, said receptacle being at the end of an arm prosthesis.

3. The terminal device of claim 1 wherein the first main part comprises a circular body of length greater than width, having a cutaway portion across its interior breadth of a size operable for closely fitting an inserted toothed arcuate fore end portion of the second main part, said inserted toothed arcuate portion being in operable contact with a worm gear installed traversing the first main part within the foremost location of the cutaway portion in effecting movement of the toothed arcuate in response to turning of the worm gear.

4. The terminal device of claim 1 wherein a cable holding device is attached near the fore end of the first main part.

5. The terminal device of claim 1 wherein the implement coupling part comprises a circular bar of a dimension to fit closely within the hollow portion of the aft end of the second main part, said implement coupling port having a securing device operable at its outer surface which cooperates in releasable connection with a connection means within said hollow portion when the implement coupling port is inserted into said hollow portion.

6. The terminal device of claim 1 wherein the implement held by the implement coupling port is selected from groups consisting of cutting tools, wrenches, clamping tools, screw drivers, hammers, scrapers, brushes, pencils, awls, scoops, planes, fishing rods, and stirring devices.

7. The terminal device of claim 1 wherein the first main body and the second main body are constructed of aircraft aluminum alloy.

8. A terminal device for releasable attachment to the end of an arm prosthesis, said terminal device comprising in operable combination a structure having a first main part with a fore end and an aft end, and a second main part having a fore end and an aft end, the fore end of the first main part configured to releasably attach to the end of an arm prosthesis, the aft end of the first main part having a slot extending across its breadth from side to side and aligned with the fore-aft axial alignment of the first main part, said slot having an arcuate terminus at its deepest penetration with a turnable worm gear extending through said first main part from side to side and communicating with the slot at the arcuate terminus at the fore end of said slot with means for turning the worm gear being located on the exterior of said first main part, said fore end of said second main part having an arcuate toothed edge on the fore end inserted into, and extending across, the slot from side to side of said first main part and which is operably meshed with the said turnable worm gear which traverses through the said first main part, with a pin passed through the aft end of the first main part and the fore end of the second main part that is inserted in the slot in the first main part, said pin operable for holding the two main parts together and for providing a pivot point for lateral movement of the arcuate toothed end responding to a turning of the worm gear to change the attitude of the second main part with respect to the fore-aft axial alignment of the first main part, and a receptacle in the aft end of the second main body for receiving, and releasably holding, an implement coupling part that is on the end of an implement.

9. The terminal device of claim 8 in combination with an implement having an implement coupling part wherein the implement coupling part is fitted with a spring-loaded ball device which cooperates with a hole in the receptacle that is operable in cooperating with the spring-loaded ball device to hold the implement in the terminal device.

10. The terminal device of claim 8 wherein the first main part and the second main part are constructed of aircraft aluminum alloy.

11. The terminal device of claim 8 wherein the implement to be held by the implement coupling port is selected from groups consisting of cutting tools, wrenches, clamping tools, screw drivers, hammers, scrapers, brushes, pencils, awls, scoops, planes, fishing rods, and stirring devices.

12. The terminal device of claim 8 wherein the spring-loaded ball device is selected from the group consisting of ball pushers and detents.

* * * * *